United States Patent
Hester, Jr. et al.

[11] Patent Number: 5,708,169
[45] Date of Patent: Jan. 13, 1998

[54] 5-AMIDOMETHYL α,β-SATURATED AND -UNSATURATED 3-ARYL BUTYROLACTONE ANTIBACTERIAL AGENTS

[75] Inventors: Jackson B. Hester, Jr., Galesburg, Mich.; Steven Joseph Brickner, Ledyard, Conn.; Michael Robert Barbachyn, Kalamazoo, Mich.; Douglas K. Hutchinson, Kalamazoo, Mich.; Dana Scott Toops, Kalamazoo, Mich.

[73] Assignee: Pharmacia & Upjohn Company, Kalamazoo, Mich.

[21] Appl. No.: 708,765

[22] Filed: Sep. 5, 1996

[51] Int. Cl.$^6$ .............. C07D 413/10; C07D 307/58; C07D 307/33
[52] U.S. Cl. .............. 549/152; 540/362; 540/363; 540/950; 544/47; 544/60; 544/105; 546/214; 548/255; 548/264.4; 548/315.4; 548/364.1; 548/453; 548/466; 548/469; 548/517; 549/321
[58] Field of Search ................ 540/362, 363, 540/950; 544/47, 60, 105; 546/214; 548/255, 264.4, 315.4, 364.1, 453, 466, 469, 517; 549/321

[56] References Cited

U.S. PATENT DOCUMENTS

| | | | |
|---|---|---|---|
| 3,331,837 | 7/1967 | Lehmann | 260/239.57 |
| 3,444,178 | 5/1969 | Bachman | 260/306.8 |
| 3,446,821 | 5/1969 | Fried et al. | 260/343.6 |
| 3,496,187 | 2/1970 | Bruderlein et al. | 260/305 |
| 3,576,010 | 4/1971 | Bachman | 260/343.6 |
| 3,647,656 | 3/1972 | Srinivasan et al. | 204/158 |
| 4,346,102 | 8/1982 | Langlois et al. | 424/279 |

FOREIGN PATENT DOCUMENTS

| | | |
|---|---|---|
| 44-17901 | 3/1969 | Japan |
| 49005961 | 5/1972 | Japan |
| 57-046975 | 3/1982 | Japan |
| 57-144274 | 9/1982 | Japan |
| 57-144275 | 9/1982 | Japan |
| 57-145873 | 9/1982 | Japan |
| 59-164787 | 9/1984 | Japan |
| 60-178879 | 9/1985 | Japan |
| 63-093774 | 9/1988 | Japan |
| 01308227 | 12/1989 | Japan |
| 01313476 | 12/1989 | Japan |
| 05294952 | 11/1993 | Japan |

OTHER PUBLICATIONS

Denis et al., Bioorganic & Medicinal Chemistry Letters, vol. 4, No. 16, pp. 1925–1930 (1994).
Derwent Abstract No. 23823V (corresponding to item BA above) (1972).
Derwent Abstract No. 82641(corresponding to item AA above) (1980).
Derwent Abstract No. 30003S (corresponding to item AB above) (1971).
Derwent Abstract No. 10949R (corresponding to item AC above) (1970).
Derwent Abstract No. 86917R (corresponding to item AD above) (1972).
Derwent Abstract No. 39256 (corresponding to item BB above) (1969).
Derwent Abstract No. 37828 (corresponding to item AE above) (1969).
Derwent Abstract No. 37486 (corresponding to item AF above) (1969).
Derwent Abstract No. 17023 (corresponding to item AG above) (1967).
Derwent Abstract No. 33807 (corresponding to item BC above) (1982).
Derwent Abstract No. 87082 (corresponding to item BD above) (1982).
Derwent Abstract No. 87083 (corresponding to item BE above) (1982).
Derwent Abstract No. 88837 (corresponding to item BF above) (1982).
Derwent Abstract No. 84–267393 (corresponding to item BG above) (1984).
Derwent Abstract No. 86–030961 (corresponding to item BH above) (1985).
Derwent Abstract No. 88–152073 (corresponding to item BI above) (1988).
Derwent Abstract No. 90–028213 (corresponding to item BJ above) (1989).
Derwent Abstract No. 90–034400 (corresponding to item BK above) (1989).
Derwent Abstract No. 93–392644 (corresponding to item BL above) (1993).

*Primary Examiner*—Bernard Dentz
*Attorney, Agent, or Firm*—Martha A. Gammill

[57] ABSTRACT

The present invention provides for new 5-amidomethyl, α,β-saturated and—unsaturated butyrolactone antibacterial agents of formula I

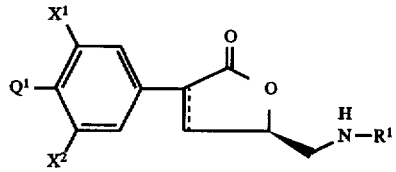

characterized by 3-aryl substituents that include, for example, indolinyl and phenyl substituted with zero (0) to two(2) halogen atoms and substituted in the para position with, e.g., piperazinyl, thiomorpholinyl (and corresponding sulfoxide and sulfone), thiazolidinyl (and sulfoxide and sulfone), morpholinyl, azetidinyl, pyrrolidinyl, piperidinyl, pyrrolyl, azepinyl, troponyl, 3,7-diazabicyclo[3.3.0]octan-3-yl, bridged thiazinyl or bridged oxazinyl moieties. In those cases where a ring nitrogen is present, then this is substituted to form an amide, formamide, sulfonamide, urethane, or alkylated with a wide variety of moieties. These compounds are effective against a number of human and veterinary pathogens, including gram-positive aerobic bacteria such as multiply-resistant *staphylococci, streptococci* and *enterococci*, as well as anaerobic organisms such as *Bacteroides spp.* and *Clostridia spp.* species, and acid-fast organisms such as *Mycobacterium tuberculosis, Mycobacterium avium* and *Mycobacterium spp.*, and in organisms such as *Mycoplasma spp.*

9 Claims, No Drawings

5-AMIDOMETHYL α,β-SATURATED AND -UNSATURATED 3-ARYL BUTYROLACTONE ANTIBACTERIAL AGENTS

CROSS-REFERENCE TO RELATED APPLICATIONS

This application claims the benefit of provisional application U.S. Ser. No. 60/003,837, filed 15 Sep. 1995, under 35 USC 119(e)(i).

FIELD OF THE INVENTION

The present invention provides for new 5-amidomethyl, α,β-saturated and—unsaturated butyrolactone antibacterial agents characterized by 3-aryl substituents that include, for example, indolinyl and phenyl substituted with zero (0) to two(2) halogen atoms and substituted in the para position with, e.g., piperazinyl, thiomorpholinyl (and corresponding sulfoxide and sulfone), thiazolidinyl (and sulfoxide and sulfone), morpholinyl, azetidinyl, pyrrolidinyl, piperidinyl, pyrrolyl, azepinyl, troponyl, 3,7-diazabicyclo[3.3.0]octan-3-yl, bridged thiazinyl or bridged oxazinyl moieties. In those cases where a ring nitrogen is present, then this is substituted to form an amide, formamide, sulfonamide, urethane, or alkylated with a wide variety of moieties.

These compounds are effective against a number of human and veterinary pathogens, including gram-positive aerobic bacteria such as multiply-resistant *staphylococci*, *streptococci* and *enterococci*, as well as anaerobic organisms such as *Bacteroides spp.* and *Clostridia spp.* species, and acid-fast organisms such as *Mycobacterium tuberculosis*, *Mycobacterium avium* and *Mycobacterium spp.*, and in organisms such as *Mycoplasma spp.*

BACKGROUND OF THE INVENTION

A wide variety of antibiotic oxazolidinone compounds are known in the art. For example, please see the following: WO 94/13649, published 23 Jun. 1994, "Tropone-Substituted Phenyloxazolidinone Antibacterial Agents"; WO 95/07271, published 16 Mar. 1995, "Substituted Oxazine and Thiazine Oxazolidinones Antimicrobials"; WO 96/15130, published 23 May 1996, "Bicyclic Oxazine and Thiazine Oxazolidinone Antibacterials"; WO 96/13502, published 9 May 1996, "Phenyloxazolidinone Antimicrobials"; WO 93/23384, published 25 Nov. 1993, "Oxazolidinone Antimicrobials Containing Substituted Diazine Moieties"; WO 90/02744, published 22 Mar. 1990; U.S. Pat. No. 5,164,510; U.S. Pat. No. 5,225,565; U.S. Pat. No. 5,182,403; "5'-Indolinyl-5β-Amidomethyloxazolidin-2-ones"; WO 95/25106, published 21 Sep. 1995, "Oxazolidinone Derivatives and Pharmaceutical Compositions Containing Them"; WO 93/09103, published 13 May 1993, "Substituted Aryl and Heteroaryl-Phenyloxazolidinones"; WO 95/14684, published 1 Jun. 1995, "Esters of Substituted Hydroxyacetyl-Piperazine Phenyl Oxazolidinones"; PCT/US96/05202, filed 18 Apr. 1996, "Spirocyclic and Bicyclic Diazinyl and Carbazinyl Oxazolidinones"; U.S. Pat. Nos. 5,231,188 and 5,247,090, "Tricyclic [6,6,5]-Fused Oxazolidinone Antibacterial Agents;" and WO 96/23788, published 8 Aug. 1996, "Hetero-Aromatic Ring Substituted Phenyloxazolidinone Antimicrobials."

"Palladium-Catalyzed Cross Coupling of Tropolone Triflates with Arylboronic Acids. An Application to the Synthesis of Tropone-Substituted Oxazolidinone (Tropox) Antibacterial Agents," Poster Presentation, 8th International Symposium on Organometallic Chemistry Directed Towards Organic Synthesis (OMCOS 8 Symposium), Santa Barbara, Calif., 6–10 Aug. 1995, disclosed an oxazolidinone compound having a 2-phenyl-tropone substituent.

Nowhere do these patents, applications or publications teach or suggest saturated and unsaturated 3-aryl butyrolactone-type compounds of the present invention.

INFORMATION DISCLOSURE

Bioorganic & Medicinal Chemistry Letters, Vol. 4, p. 1925 (1994), "5-Aryl-β,γ Butenolide, A New Class of Antibacterial Derived from the N-Aryl Oxazolidinone DUP 721," discloses a 5-aryl-β,γ butenolide which has antibiotic activity.

The compounds of the present invention are new saturated and unsaturated 3-aryl butyrolactone antibacterial agents having a 3-phenyl (e.g., monofluoro, difluoro, desfluoro) group, wherein the pheyl group is also substituted at the para position with various heterocyclic rings. In contrast, the prior art discloses p-acetyl substitution of the phenyl ring.

The following references disclose compounds which are structurally different from the compounds of the present invention:

Derwent Abstract 23823V discloses α,β unsaturated γ-butyrolactones which are useful as bactericides.

Derwent Abstract 82641 discloses 3-substituted phenyl-5-hydroxymethyl-furan-2-one derivatives and their precursors which are useful as antidepressants and for treating senility.

Derwent Abstract 30003S discloses antibacterial 2-(substituted nitro-anilino and toluidino)-4,4,-dihalofuran-5-ones.

Derwent Abstract 10949R discloses amoebicial and antibacterial compositions containing novel N-thiazolyl N-thiadiazolyl and N-benzothiazoyl aconamides.

Derwent Abstract 86917R discloses photoisomerisation of α-alkoxy or aryloxy furan compounds to form α-substituted, β, γ-unsaturated lactones, such as 2-oxo-3-methyl-2,3-dihydrofuran, including numerous biologically active natural products.

Derwent Abstract 39,256 discloses the preparation of 3-phenyl-4-hydroxy-2(5H)-furanone, antibiotic.

Derwent Abstract 37,828 discloses α-amino or hydroxy-β-triarylmethyl-mercaptomethyl α, β-butenolides, which may have antibacterial activity.

Derwent Abstract 37,486 discloses halogenated 2-(2-thiazolyl)aminofuran-5-ones, antibacterial agents.

Derwent Abstract 17,023 discloses γ-lactones which are optionally substituted with hydrocarbon residues, such as β:γ:γ-triphenylbutenolide and which possess antibacterial and antibiotic properties.

Derwent Abstract 33807 discloses substituted delta alpha, beta, or delta beta, gamma butenolides such as α-benzyl-Δ, α, β butenolide, having insecticidal and bactericidal activities.

Derwent Abstract 87082 discloses five-membered cyclic unsaturated lactone compounds which are starting materials for pharmaceuticals and agrochemicals.

Derwent Abstract 87083 discloses 5-alkoxy-3,4-optionally disubstituted-2(5H)-furanone compounds, such as 5-ethoxy-3,4-diphenyl-2(5H)-furanone, which are starting materials for pharmaceuticals or agrochemicals.

Derwent Abstract 88837 discloses muscle relaxing furfural derivatives.

Derwent Abstract 84-267393 discloses 5-membered cyclic unsaturated lactones which are raw materials for drugs or agrochemicals.

Derwent Abstract 86-030961 discloses new furanone derivatives and pharmaceutically acceptable salts which are useful for the treatment of diabetic complications.

Derwent Abstract 88-152073 discloses 4-amino-2-(5H)-furanone derivatives, such as 4-amino-5,5-di-methyl-2(5H)-furanone, which are intermediates in preparing 2-furanone derivatives exhibiting physiological activities, such as antitumor, bactericidal or antihypertensive action.

Derwent Abstract 90-028213 discloses new substituted 3-pyrroline derivatives and corresponding oxygen- and sulfur-containing heterocyclic compounds, such as 2-(hexadecylthio)-3-hydroxy-4-phenyl-2-buten-4-olide, which are elastase and protease inhibitors promoting healing and to protect against infectious diseases.

Derwent Abstract 90-034400 discloses new 3-O-acyl-5,6-O-benzylidene-ascorbic acids, such as 5,6,O-benzylidene-3-O-[5,7,7-trimethyl-2-(1,3,3-trimethylbutyl)]octanoyl-ascorbic acid, having tumor cell growth inhibitory activity and good cell membrane permeability.

Derwent Abstract 93-392644 discloses antibiotics WAP-4068 and its derivatives for treatment of fungal infections, which are prepared by incubating Pseudomonas microorganism.

SUMMARY OF THE INVENTION

The present invention particularly provides:

A compound of the formula I

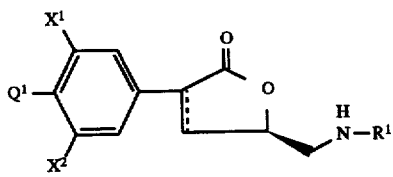

I wherein — is a single or double bond;
wherein $X^1$ and $X^2$ are independently
  —H,
  —F, or
  —Cl;
wherein $Q^1$ is:

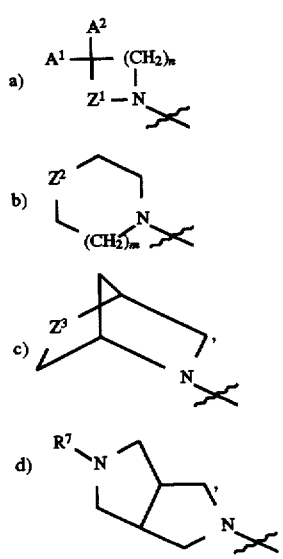

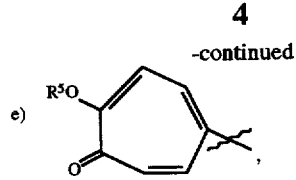

VI

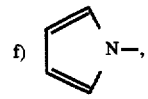   VII

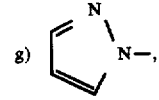   VIII

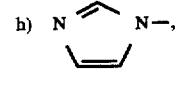   IX

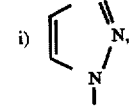   X

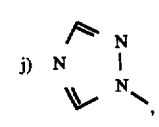   XI

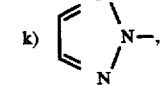   XII

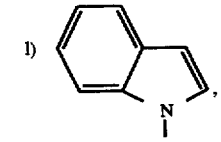   XIII

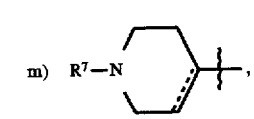   XIV $Q^1$ and $X^2$ taken together are

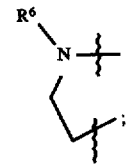   XV wherein $Z^1$ is
  a) —CH$_2$—,
  b) —CH(R$^4$)—CH$_2$—,
  c) —C(O)—, or
  d) —CH$_2$CH$_2$CH$_2$—;
wherein $Z^2$ is
  a) —O$_2$S—,
  b) —O—,
  c) —N(R$^7$)—,
  d) —OS—, or
  e) —S—;
wherein $Z^3$ is
  a) —O$_2$S—, b) —O—,
c) —OS—, or
d) —S—;
wherein A¹ is
a) H—, or
b) CH₃;
wherein A² is
a) H—,
b) HO—,
c) CH₃—,
d) CH₃O—,
e) R²O—CH₂—C(O)—NH—,
f) R³O—C(O)—NH—,
g) (C₁-C₂)alkyl—O—C(O)—,
h) HO—CH₂—,
i) CH₃O—NH—,
j) (C₁-C₃)alkyl—O₂C—
k) CH₃—C(O)—,
l) CH₃—C(O)—CH₂—, m) 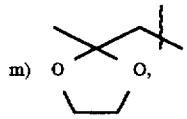

n) 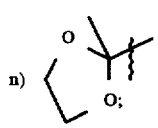

A¹ and A² taken together are:

a) 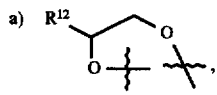

b) O=, or c) 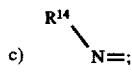

wherein R¹ is
a) —CHO,
b) —COCH₃,
c) —COCHCl₂,
d) —COCHF₂,
e) —CO₂CH₃,
f) —SO₂CH₃, or
g) —COCH₂OH;
wherein R² is
a) H—,
b) CH₃—,
c) phenyl-CH₂—, or
d) CH₃C(O)—;
wherein R³ is
a) (C₁-C₃)alkyl-, or
b) phenyl-;
wherein R⁴ is
a) H—, or
b) HO—;
wherein R⁵ is
a) H—,
b) (C₁-C₃)alkyl-,
c) CH₂=CH—CH₂—, or
d) CH₃—O—(CH₂)₂—;
wherein R⁶ is
a) CH₃—C(O)—,
b) H—C(O)—,
c) Cl₂CH—C(O)—,
d) HOCH₂—C(O)—,
e) CH₃SO₂—, f)  XXI g) F₂CHC(O)—, h) 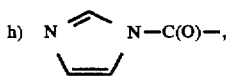 XXII i) H₃C—C(O)—O—CH₂—C(O)—,
j) H—C(O)—O—CH₂—C(O)—, k) 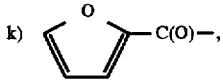 XXIII l) HC≡C—CH₂O—CH₂—C(O)—, or
m) phenyl—H₂—O—CH₂—C(O)—;
wherein R⁷ is
a) R²O—C(R₁₀)(R₁₁)—C(O)—,
b) R³O—C(O)—,
c) R⁸—C(O)—, d)  XXIV e)  XXV f) H₃C—C(O)—(CH₂)₂—C(O)—,
g) R⁹—SO₂—, h) 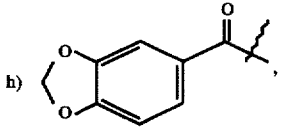 XXVI i) HO—CH₂—C(O)—,
j) R¹⁶—(CH₂)₂—,
k) R¹³—C(O)—O—CH₂—C(O)—,
l) (CH₃)₂N—CH₂—C(O)—NH—,
m) NC—CH₂—, or
n) F₂—CH—CH₂—;
wherein R⁸ is
a) H—,
b) (C₁-C₄)alkyl,
c) aryl-(CH₂)ₚ,
d) ClH₂C—,
e) Cl₂HC—, f) FH$_2$C—, g) F$_2$HC—, or h) (C$_3$–C$_6$)cycloalkyl;

wherein R$^9$ is a) —CH$_3$, b) —CH$_2$Cl c) —CH$_2$CH=CH$_2$, d) aryl, or e) —CH$_2$CN;

wherein R$^{10}$ and R$^{11}$ are independently a) H—, b) CH$_3$—; or wherein R$^{12}$ is a) H—, b) CH$_3$O—CH$_2$O—CH$_2$—, or c) HOCH$_2$—;

wherein R$^{13}$ is a) CH$_3$—, b) HOCH$_2$—, c) (CH$_3$)$_2$N-phenyl, or d) (CH$_3$)$_2$N—CH$_2$—;

wherein R$^{14}$ is a) HO—, b) CH$_3$O—, c) H$_2$N—, d) CH$_3$O—C(O)—O—, e) CH$_3$—C(O)—O—CH$_2$—C(O)—O—, f) phenyl-CH$_2$—O—CH$_2$—C(O)—O—, g) HO—(CH$_2$)$_2$—O—, h) CH$_3$O—CH$_2$—O—(CH$_2$)$_2$—O—, or i) CH$_3$O—CH$_2$—O—;

wherein R$^{15}$ is a) H—, or b) Cl—;

wherein R$^{16}$ is a) HO— b) CH$_3$O—, or c) F;

wherein m is zero (0) or one (1);

wherein n is one (1) to three (3), inclusive;

wherein p is zero (0) or one (1);

wherein aryl is phenyl substituted with zero (0) or one (1) of the following:

a) —F, b) —Cl, c) —OCH$_3$, d) —OH, e) —NH$_2$, f) —(C$_1$–C$_4$)alkyl, g) —O—C(O)—OCH$_3$, or h) —NO$_2$;

or pharmaceutically acceptable salts thereof.

The present invention more particularly provides:

The compound of claim 1 with the following provisos:

1) in the moiety of formula II, when Z$^1$ is —CH$_2$— or —C(O)—, n is one (1);

2) in the moiety of formula II, when Z$^1$ is —CH$_2$—CH$_2$—CH$_2$—, n is not three (3);

The compound of claim 1 wherein Q$^1$ is the moiety of formula II;

The compound of claim 1 wherein Q$^1$ is the moiety of formula III;

The compound of claim 1 wherein Q$^1$ is the moiety of formula IV;

The compound of claim 1 wherein Q$^1$ is the moiety of formula V;

The compound of claim 1 wherein Q$^1$ is the moiety of formula VI;

The compound of claim 1 wherein Q$^1$ is the moiety of formula VII, VIII, IX, X, XI, XII, XIII, or XIV;

The compounds of the present invention are named according to the IUPAC or CAS nomenclature system.

The carbon atom content of various hydrocarbon-containing moieties is indicated by a prefix designating the minimum and maximum number of carbon atoms in the moiety, i.e., the prefix C$_i$–C$_j$ indicates a moiety of the integer "i" to the integer "j" carbon atoms, inclusive. Thus, for example, (C$_1$–C$_3$)alkyl refers to alkyl of one to three carbon atoms, inclusive, or methyl, ethyl, propyl and isopropyl, straight and branched forms thereof.

Throughout this application, abbreviations which are well known to one of ordinary skill in the art may be used, such as "Ph" for phenyl, "Me" for methyl, and "Et" for ethyl. "Pharmaceutically acceptable salts" are acid addition salts of the compounds of the present invention, where appropriate as recognized by one of ordinary skill in organic chemistry, and which are prepared by any of the art recognized means. Typical, acid addition salts include hydrochloride, hydrobromide, hydroiodide, sulfate, methanesulfonates, ethanesulfonates, benzenesulfonates, toluenesulfonates, fumarates and other pharmaceutically acceptable counter ions for amines.

The following Charts I–XI describe the preparation of representative side chains and/or substituents (e.g., Q$^1$, X$^1$, X$^2$ and R$^1$) that appear off of the saturated and unsaturated 3-aryl butyrolactone ring of the compounds of the present invention. (Charts XII and XIII below describe the preparation of the saturated and unsaturated 3-aryl butyrolactone ring itself.) All of the side chains or substituents can be prepared by procedures described in the charts or by procedures analogous thereto which would be well known to one of ordinary skill in organic chemistry. The following patents, applications and publications which further describe and exemplify these procedures are hereby incorporated by reference herein: WO 95/07271, published 16 Mar. 1995; WO 96/15130, published 23 May 1996; WO 96/13502, published 9 May 1996; WO 95/25106, published 21 Sep. 1995; WO 94/13649, published 23 Jun. 1994; WO 95/14684, published 1 Jun. 1995; WO 93/23384, published 25 Nov. 1993; WO 96/23788, published 8 Aug. 1996; U.S. Pat. Nos. 5,164,510 and 5,225,565; and PCT/US96/05202, filed 18 Apr. 1996.

In the text below corresponding to these charts, the formula at the left margin corresponds to a specific Q$^1$ moiety in the charts (and in Chart VIII to a specific R$^1$) and the other variables are as defined in the charts with X$^1$ and X$^2$ most often being hydrogen or fluorine and R$^1$ most often being —COCH$_3$, for purposes of example only.

CHART I

I-A Using the general procedures from WO 95/07271, published 16 Mar. 1995, page 21, line 33, through page 23, line 32.

I-B Using the general procedures from WO 95/07271, published 16 Mar. 1995, page 16, lines 16–32, for the oxidation from I-A.

I-C Using the general procedures from WO 95/07271, published 16 Mar. 1995, page 15, line 32, through page 16, line 14, for the oxidation to the sulfone I-C from I-A.

I-D Using the procedures described for Formula I-A, but substituting oxazine for thiazolidine.

CHART II

II-A Using the general procedures from WO 95/07271, published 16 Mar. 1995, page 12, line 31, through page 15, line 30.

II-B Using the general procedures from WO 95/07271, published 16 Mar. 1995, page 16, lines 16–32, from Formula II-A.

II-C Using the general procedures from WO 95/07271, published 16 Mar. 1995, page 15, line 32, through page 16, line 14, from Formula II-A.

II-D Using the general procedures from WO 96/15130, published 23 May 1996, Example 2, page 14, line 24, through page 17, line 6.

II-E Using the general procedures from WO 96/15130, published 23 May 1996, page 10, line 7, through page 10, line 13.

II-F Using the general procedures from WO 96/15130, published 23 May 1996, Example 3, page 17, lines 8–21 from Formula II-D.

CHART III

III-A Using the general procedures from WO 95/07271, published 16 Mar. 1995, page 19, line 6, through page 21, line 13; and page 23, line 33, through page 24, line 35.

III-B Using the general procedures from WO 96/15130, published 23 May 1996, Example 1, page 12, line 1, through page 14, line 22.

CHART IV

IV-A Using the general procedures from WO 96/13502, published 9 May 1996, Example 1, Steps 2–7, at page 30, line 14, through page 33, line 2, but substituting azetidine for 1-(diphenylmethyl)-5-methoxyazetidine;

IV-B Using the general procedures from WO 96/13502, published 9 May 1996, Example 2 at page 33, line 4, through page 36, line 22; and Example 4 at page 40, lines 1–15;

IV-C Using the general procedures from WO 96/13502, published 9 May 1996, Example 2 at page 33, line 4, through page 36, line 22;

IV-D Using the general procedures from WO 96/13502, published 9 May 1996, Example 7 at page 43, line 36, through page 47, line 28;

IV-E Using the general procedures from WO 96/13502, published 9 May 1996, Example 6 at page 40, line 31, through page 43, line 34;

IV-F Starting with IV-C, and using procedures well known for methylation; e.g., NaH and dimethylsulfate in a suitable solvent;

IV-G Starting with IV-B, and using the procedures from WO 95/25106, published 21 Sep. 1995, page 23, line 36, Example 5;

IV-H Starting with IV-B, using the general procedures from WO 96/13502, published 9 May 1996, Example 5 at page 40, lines 17–29;

IV-I Starting with IV-B and treating with hydrazine hydrate in ethanol by procedures well-known in the art;

IV-J Using procedures described in WO 96/13502, published 9 May 1996, on page 70, Chart VII, and in text, page 13, lines 12–26;

IV-K Using procedures described in WO 96/13502, published 9 May 1996, on page 70, Chart VII, $R_{18}$ or $R_{19}$ is OH, and in text, page 13, lines 12–26;

IV-L Using the procedures from WO 95/25106, published 21 Sep. 1995, Compound No. 42, page 41, line 28, through page 42, line 4;

IV-M Using the procedures from WO 95/25106, published 21 Sep. 1995, Compound No. 47, page 43, lines 17–26;

IV-N Using the procedures from WO 95/25106, published 21 Sep. 1995, Compound No. 49, page 44, lines 5–15;

IV-O Using the procedures from WO 95/25106, published 21 Sep. 1995, Compound No. 52, page 45, lines 1–13;

IV-P Using the procedures from WO 95/25106, published 21 Sep. 1995, and reducing the compound of VI-G;

IV-Q Using the procedures from WO 95/25106, published 21 Sep. 1995, Compound No. 57, page 46, lines 24–34;

IV-R Using the procedures from WO 95/25106, published 21 Sep. 1995, Compound No. 64, page 49, lines 3–14.

CHART V

V-A Using the procedure from WO 95/25106, published 21 Sep. 1995, page 42, Example 1, but using pyrrolidine instead of piperidine;

V-B As described in WO 96/13502, published 9 May 1996, in Chart XI and XII at pages 71 and 72 and in the text (Example 11) at page 53, line 32, through page 56, line 17;

V-C As described in WO 96/13502, published 9 May 1996, in Example 10 at page 50, line 25, through page 53, line 30;

V-D As described in WO 96/13502, published 9 May 1996, starting with Formula V-C and using standard acylation procedures; e.g., acetic anhydride in pyridine;

V-E As described in WO 96/13502, published 9 May 1996, in Examples 8 and 9 at page 47, line 30, through page 50, line 23;

V-F Starting with V-B, using the procedures from WO 95/25106, published 21 Sep. 1995, page 48, Example 5;

V-G Starting with V-B, using the general procedures from WO 96/13502, published 9 May 1996, in Example 5 at page 40, lines 17–29;

V-H Starting with V-B and treating with hydrazine hydrate in ethanol using procedures well-known in the art;

V-I Wherein $R^2$ is H; using the procedure described in WO 96/13502, published 9 May 1996, in Examples 12 and 13 at page 56, line 19, through page 59, line 4;

V-I Wherein $R^2$ is methyl; 3-amino-pyrrolidin-1-yl is prepared using the procedure described in WO 96/13502, published 9 May 1996, in Example 12 at page 56, line 19, through page 58, lines 17–19; acylate 3-amino-pyrrolidin-1-yl with methoxy acetyl chloride by methods known in the art.

V-J Wherein $R^3$ is methyl, ethyl, or propyl; acylate 3-amino-pyrrolidin-1-yl with methylchloroformate, ethylchloroformate, or propylchloroformate, respectively, by methods known in the art; 3-amino-pyrrolidin-1-yl is prepared using procedures described in WO 96/13502, published 9 May 1996, in Example 12 at page 56, line 19, through page 58, lines 17–19;

V-K Using the procedures from WO 95/25106, published 21 Sep. 1995, Compound No. 42, page 41, line 28, through page 42, line 4;

V-L Using the procedures from WO 95/25106, published 21 Sep. 1995, Compound No. 47, page 43, lines 17–26;

V-M Using the procedures from WO 95/25106, published 21 Sep. 1995, Compound No. 49, page 44, lines 5–15;

V-N Using the procedures from WO 95/25106, published 21 Sep. 1995, Compound No. 52, page 45, lines 1–13;

V-O Using the procedures from WO 95/25106, published 21 Sep. 1995, and reducing the compound of VI-G above;

V-P Using the procedures from WO 95/25106, published 21 Sep. 1995, Compound No. 61, page 48, lines 4–13;

V-Q Using the procedures from WO 95/25106, published 21 Sep. 1995, Compound No. 57, page 46, lines 24–34;

V-R Using the procedures from WO 95/25106, published 21 Sep. 1995, page 28, line 26, through page 29, line 5, Example 14;

V-S Using the procedures from WO 95/25106, published 21 Sep. 1995, Compound No. 64, page 49, lines 3–14;

V-T Using the procedures from WO 95/25106, published 21 Sep. 1995, Compound No. 30, page 37, lines 24–35.

CHART VI

VI-A Using the general procedures from WO 95/25106, published 21 Sep. 1995, page 20, line 27, through page 22, line 5, Example 1;

VI-B Using the general procedures from WO 95/25106, published 21 Sep. 1995, page 22, lines 21–35, Example 3;

VI-C Using the general procedures from WO 95/25106, published 21 Sep. 1995, page 34, lines 2–13, Compound No. 3, made from VI-B by sodium borohydride reduction;

VI-D Using the general procedures from WO 95/25106, published 21 Sep. 1995, page 22, lines 6–20, Example 2;

VI-E Wherein $R^4$ is hydrogen, using the procedure described in WO 95/25106, published 21 Sep. 1995, Compound No. 8, page 35, line 29, through page 36, line 5;

VI-E Wherein $R^4$ is methyl or ethyl, esterify the compound of VI-E, wherein $R^4$ is hydrogen, using hydrogen chloride gas dissolved in methanol or ethanol, respectively.

VI-F Using the procedures from WO 95/25106, published 21 Sep. 1995, page 23, lines 25–36, Example 5;

VI-G Using the procedures from WO 95/25106, published 21 Sep. 1995, page 29, line 30, through page 30, line 8, Example 16;

VI-H Using the procedures from WO 95/25106, published 21 Sep. 1995, react the compound of VI-B with hydrazine in ethanol using procedures well-known in the art;

VI-I Using the procedures from WO 95/25106, published 21 Sep. 1995, page 22, lines 21–35, Example 3, but starting with 3-piperidinone VI-J Starting with the compound of VI-I, perform a sodium borohydride reduction.

VI-K Using the procedures from WO 95/25106, published 21 Sep. 1995, page 23, lines 25–36, Example 5, but starting with 3-piperidinone.

VI-L Using the procedures from WO 95/25106, published 21 Sep. 1995, page 29, line 30, through page 30, line 8, Example 16, but starting with 3-piperidinone.

VI-M Using the procedures from WO 95/25106, published 21 Sep. 1995, react the compound of Formula VI-I with hydrazine in ethanol;

VI-N Using the alkylation procedures from WO 95/25106, published 21 Sep. 1995, Compound No. 29, page 37, lines 13–22;

VI-O Using the procedures from WO 95/25106, published 21 Sep. 1995, Compound No. 30, page 37, lines 23–35;

VI-P Using the procedures from WO 95/25106, published 21 Sep. 1995, Compound No. 32, page 38, lines 12–26;

VI-Q Starting from the compound of formula VI-S, and using procedures from WO 95/25106, published 21 Sep. 1995, Compound No. 35, page 39, lines 15–29;

VI-R Using the procedures from WO 95/25106, published 21 Sep. 1995, Compound No. 10, page 36, lines 20–32;

VI-S Using the procedures from WO 95/25106, published 21 Sep. 1995, Example 7, page 24, lines 11–34;

VI-T Using the procedures from WO 95/25106, published 21 Sep. 1995, Example 11, page 26, line 36, through page 28, line 7;

VI-U Using the procedures from WO 95/25106, published 21 Sep. 1995, Compound No. 40, page 41, lines 2–16;

VI-V Using the procedures from WO 95/25106, published 21 Sep. 1995, Compound No. 42, page 41, line 28, through page 42, line 4;

VI-W Using the procedures from WO 95/25106, published 21 Sep. 1995, Compound No. 47, page 43, lines 17–26;

VI-X Using the procedures from WO 95/25106, published 21 Sep. 1995, Compound No. 49, page 44, lines 5–15;

VI-Y Using the procedures from WO 95/25106, published 21 Sep. 1995, Compound No. 52, page 45, lines 1–13;

VI-Z Using the procedures from WO 95/25106, published 21 Sep. 1995, and reducing the compound of VI-G;

VI-A-1 Using the procedures from WO 95/25106, published 21 Sep. 1995, Compound No. 61, page 48, lines 4–13;

VI-B-1 Using the procedures from WO 95/25106, published 21 Sep. 1995, Compound No. 57, page 46, lines 24–34;

VI-C-1 Using the procedures from WO 95/25106, published 21 Sep. 1995, page 28, line 26, through page 29, line 5, Example 14;

VI-D-1 Using the procedures from WO 95/25106, published 21 Sep. 1995, Compound No. 64, page 49, lines 3–14;

VI-E-1 Using the procedures from WO 95/25106, published 21 Sep. 1995, Compound No. 30, page 37, lines 24–35.

CHART VII

VII-A Prepared preferably by treating the compound VII-B with water in the presence of trifluoroacetic acid;

VII-B Which is an enantiomer wherein both $X^1$ and $X^2$ are hydrogen, prepared by following the procedures analogous to those described in WO 94/13649, published 23 Jun. 1994, page 47, lines 4–21, Example 6;

VII-B Which is an enantiomer wherein both $X^1$ and $X^2$ are fluorine, prepared by following the procedures described in WO 94/13649, published 23 Jun. 1994, page 51, line 24, through page 52, line 7, Example 11;

VII-B Which is a racemic mixture wherein both $X^1$ and $X^2$ are hydrogen, prepared by following the procedures described in WO 94/13649, published 23 Jun. 1994, pages 39, line 17, through page 40, line 1, Example 1;

VII-C Prepared by following the procedures described in WO 94/13649, published 23 Jun. 1994, on page 46, line 18, through page 47, line 1, Example 5;

VII-D Prepared by using procedures described for VII-C described above;

VII-E Prepared by using procedures described for VII-C described above;

VII-F Prepared by using procedures described for VII-C described above.

CHART VIII

VIII-A Following the procedures of U.S. Pat. No. 5,164,510, Examples 1–8;

VIII-B Following the procedures of U.S. Pat. No. 5,164,510, Example 21;

VIII-C Following the procedures of U.S. Pat. No. 5,164,510, Example 23;

VIII-D Following the procedures of U.S. Pat. No. 5,164,510, Example 150;

VIII-E Following the procedures of U.S. Pat. No. 5,164,510, Example 148;

VIII-F Following the procedures of U.S. Pat. No. 5,164,510, Examples 145 and 146;

VIII-G Following the procedure of U.S. Pat. No. 5,164,510, procedures 145 and 146;

VIII-H Following the procedures of U.S. Pat. No. 5,164,510, using Example 23;

VIII-I Following the procedures of U.S. Pat. No. 5,164,510, using Formula II in this patent, wherein R' is hydrogen, treat with carbonyldiimidazole;

VIII-J Following the procedures of U.S. Pat. No. 5,164,510, Examples 143 and 144;

VIII-K Treat the compound VIII-D with mixture of formic acid and acetic anhydride;

VIII-L Following the procedures of U.S. Pat. No. 5,164,510, using Examples 145 and 146, except substituting 2-furancarboxylic acid chloride for the 2-thienyl carboxylic acid chloride;

VIII-M Treating VIII-D with NaH and propargyl bromide;

VIII-N Following the procedures of U.S. Pat. No. 5,164,510, Example 151;

VIII-O Following the procedures of U.S. Pat. No. 5,164,510, using 145 and 146, but substituting 5-chloro-thienyl-carboxylic acid chloride for thenyl-carboxylic acid chloride;

VIII-P For $R^1$—Following the procedures of U.S. Pat. No. 5,225,565, Example 49;

VIII-Q For $R^1$—Following the procedures of U.S. Pat. No. 5,225,565, Example 46;

VIII-R For $R^1$—Following the prcedures of U.S. Pat. No. 5,225,565, but substituting the respective acid halide desired for acetic anhydride;

VIII-S For $R^1$—Following the procedures of U.S. Pat. No. 5,225,565, but substituting the respective acid halide desired for acetic anhydride;

VIII-T For $R^1$—Following the procedures of U.S. Pat. No. 5,225,565, Example 51.

VIII-U For $R^1$—Under standard procedures, using mesyl-chloride with triethylamine in THF at 0° C.

VIII-V Following the procedures of WO 95/14684, published 1 Jun. 1995; and WO 90/02744, published 22 Mar. 1990; U.S. Pat. No. 5,164,510; U.S. Pat. No. 5,225,565; U.S. Pat. No. 5,182,403.

CHART IX

IX-A Using the general procedures from WO 95/14684, published 1 Jun. 1995, page 9, lines 1–14;

IX-B Using the general procedures from W0 95/14684, published 1 Jun. 1995, page 9, lines 1–28;

IX-C Using the general procedures from WO 93/23384, published 25 Nov. 1993, page 23, lines 4–17;

IX-D Using the general procedures from WO 93/23384, published 25 Nov. 1993, page 25, lines 13–25;

IX-E Using the general procedures from WO 93/23384, published 25 Nov. 1993, page 19, lines 26–33

IX-F Using the general procedures from WO 93/23384, published 25 Nov. 1993, page 18, lines 10–26;

IX-G Using the general procedures from WO 95/14684, published 1 Jun. 1995, page 14, line 26, through page 15, line 5;

IX-H Using the general procedures from WO 95/14684, published 1 Jun. 1995,

IX-I Using the general procedures from WO 95/14684, published 1 Jun. 1995,

IX-J Using the general procedures from WO 95/14684, published 1 Jun. 1995,

IX-K Using the general procedures from WO 95/14684, published 1 Jun. 1995, page 12, lines 19–31;

IX-L Using the procedures described in WO 93/23384, published 25 Nov. 1993,

IX-M Using the procedures described in WO 93/23384, published 25 Nov. 1993,

IX-N Using the procedures described in WO 93/23384, published 25 Nov. 1993,

IX-O Using the general procedures from WO 95/14684, published 1 Jun. 1995, page 25, lines 1–23;

IX-P Using the general procedures from WO 95/14684, published 1 Jun. 1995, procedure 2, page 12, lines 11–17;

IX-Q Using the general procedures from WO 95/14684, published 1 Jun. 1995, procedure 3, page 27, lines 20–35;

IX-R Using the general procedures from WO 93/23384, published 25 Nov. 1993,

IX-S Using the general procedures from WO 93/23384, published 25 Nov. 1993,

IX-T Using the general procedures from WO 93/23384, published 25 Nov. 1993,

IX-U Using the procedures from WO 93/23384, published 25 Nov. 1993, Example 9, page 17, line 33, through page 18, line 8;

IX-V Using the procedures from WO 93/23384, published 25 Nov. 1993,

IX-W Using the procedures from WO 93/23384, published 25 Nov. 1993,

IX-X Using the general procedures from WO 93/23384, published 25 Nov. 1993, page 23, lines 19–27;

IX-Y Using the general procedures from WO 93/23384, published 25 Nov. 1993, page 15, line 25, through page 16, line 2;

IX-Z Using the general procedures from WO 93/23384, published 25 Nov. 1993, page 23, line 35, through page 24, line 3;

IX-A-1 Using the general procedures from WO 93/23384, published 25 Nov. 1993, page 32, lines 11–21, Example 39;

IX-B-1 Using the general procedures from WO 93/23384, published 25 Nov. 1993, page 31, lines 9–33, Examples 36 and 37.

CHART X

X-A Using the general procedures from WO 95/25106, published 21 Sep. 1995, page 22, lines 21–35, Example 3; Example 16, but starting with 3-piperidinone.

X-B Using the procedures from WO 95/25106, published 21 Sep. 1995, page 29, line 30, through page 30, line 8, Example 16, but starting with 3-piperidinone;

X-C Using the procedures from WO 95/25106, published 21 Sep. 1995, page 23, lines 25–36, Example 5, but starting with 3-piperidinone.

X-D Starting with the compound X-A above, perform a sodium borohydride reduction;

X-E Using the alkylation procedures from WO 95/25106, published 21 Sep. 1995, Compound No. 29, page 37, lines 13–22;

X-F Using the procedures from WO 95/25106, published 21 Sep. 1995, Compound No. 30, page 37, lines 23–5;

CHART XI

XI-A Using the procedures from WO 96/23788, published 8 Aug. 1996, Example 1, pages 17–19;

XI-B Using the procedures from WO 96/23788, published 8 Aug. 1996, Example 2, pages 19–21;

XI-C Using the procedures from WO 96/23788, published 8 Aug. 1996, Example 3, pages 21–23;

XI-D Using the procedures from WO 96/23788, published 8 Aug. 1996, Examples 2–4, pages 19–25, and page 14, lines 26–27; separated from the compound of XI-F, after the first step, by chromatographic means known in the art; thereafter carried to final product following procedures described in Examples 2–4;

XI-E Using the procedures from WO 96/23788, published 8 Aug. 1996, Example 4, pages 23–25;

XI-F Using the procedures from WO 96/23788, published 8 Aug. 1996, Examples 2–4, pages 19–25; separated from the compound of XI-D after the first step by chromatographic methods known in the art; thereafter carried to final product following procedures described in Examples 2–4;

XI-G Using the procedures from WO 96/23788, published 8 Aug. 1996, Example 5, pages 25–27.

CHART XII

The following is a description of the synthesis of a morpholine fluorophenyl-acetic acid derivative which is used as an intermediate for the synthesis of the saturated and unsaturated 3-aryl butyrolactone analog of Formula XII-L in Chart XII.

The starting material is commercially available 3,4-difluorobenzoic acid of formula XII-A. The acid is converted to its methyl ester via standard acid catalyzed esterification (MeOH, HCl (g)). The crude ester is treated with morpholine (excess) of formula XII-B in DMSO with heating to give the morpholine substituted methyl benzoate derivative of formula XII-C. The ester is cleanly reduced with lithium aluminun hydride in THF to give the alcohol of formula XII-D.

There are many methods available for the direct conversion of alcohols to bromides. The alcohol is treated with HBr (J. Org. Chem. 52 5560 (1987); J. Am. Chem. Soc. 109 3098 (1987)) to give the benzylic bromide of formula XII-E. Alternatively the alcohol is treated with $PBr_3$ (J. Am. Chem. Soc. 98 4925 (1976); 107 2712 (1985)) or the combination of $Ph_3P/CBr_4$ (J. Am. Chem. Soc. 109 2738 (1987)) to give the desired bromide of formula XII-E.

From the bromide, there are two directions along which the synthesis can proceed. One method involves formation of the Grignard of formula XII-F from the bromide (or halogen metal exchange with n-BuLi to give the benzyllithium), followed by reaction with $CO_2$. Acidic work-up provides the desired (3-fluoro-4-morpholinyl)-phenyl acetic acid intermediate of formula XII-H. Alternatively, nucleophilic displacement of the bromide with CN, gives the desired intermediate of formula XII-G upon hydrolysis of the nitrile to the acid of formula XII-H.

The synthesis of the saturated and unsaturated 3-aryl butyrolactone ring system parallels that described in *Bioorganic & Medicinal Chemistry Letters*, Vol. 4, No. 16, pp. 1925–1930 (1994). The lithiated dianion of the (3-fluoro-4-morpholinyl)-phenyl acetic acid intermediate of formula XII-H is reacted with commercially available (R)-benzyloxymethyloxirane of formula XII-I in THF. The resulting γ-hydroxyacid is cyclized with catalytic p-toluene sulfonic acid in toluene with azeotropic removal of water. The lactone of formula XII-J is obtained as a mixture of diastereomers. At this stage the N-acetyl functionality is introduced by a sequence of hydrogenolytic benzyl deprotection, mesylate formation, nucleophilic substitution by azide ion, hydrogenolytic reduction and acetyl formation with acetic anhydride. This intermediate of formula XII-K is converted to the saturated and unsaturated 3-aryl butyrolactone of formula XII-L in the same manner as the tropone saturated and unsaturated 3-aryl butyrolactone, described in the Preparations and Examples below. This material is then brominated with NBS (N-bromosuccinimide), and the double bond introduced by elimination with dry pyridine in toluene with heating.

This synthesis of the saturated and unsaturated 3-aryl butyrolactone compounds of the present invention in which $Q^1$ is any of the other groups previously described is carried out similarly. During the synthesis, suitable protecting groups may be used on the side chains and/or substituents off of the ring as appropriate and as well known to one of ordinary skill in organic chemistry.

It will be apparent to those skilled in the art that the described synthetic procedures are merely representative in nature and that alternative synethetic processes are known to one of ordinary skim in organic chemistry.

The saturated and unsaturated 3-aryl butyrolactone compounds of the present invention have useful activity against a variety of organisms. The in vitro activity of compounds of the present invention are assessed by standard testing procedures such as the determination of minimum inhibitory concentration (MIC) by agar dilution as described in "Methods for Dilution Antimicrobial Susceptiblity Tests for Bacteria That Grow Aerobically" (MFT) published January 1993 by the National Committee for Clinical Laboratory Standards. (NCCLS), 771 East Lancaster Avenue, Villanova, Pa. 19084 USA. The activity of selected compounds of the present invention against *Staphylococcus aureus* and *Streptococcus pneumoniae* are shown in Table 1.

TABLE 1

| Compound of Example No. | MIC (µg/mL) *Staphylococcus Aureus* 9213 | MIC (µg/mL) *Staphylococcus Pneumoniae* 9912 | Vancomycin MIC (µg/mL) |
|---|---|---|---|
| 1 | 2 | <0.5 | 1 |

Antimicrobial activity was tested in vivo using the Murine Assay procedure. Groups of female mice (six mice of 18–20 grams each) are injected intraperitoneally with bacteria which is thawed just prior to use and suspended in brain heart infusion with 4% brewer's yeast (*Staphylococcus aureus*) or brain heart infusion (*Streptococcus species*). Antibiotic treatment at six dose levels per drug is administered one hour and five hours after infection by either oral intubation or subcutaneous routes. Survival is observed daily for six days. $ED_{50}$ values based on mortality ratios are calculated using probit analysis. The subject compounds are compared against well-known antimicrobials as controls. The data for the compounds of the present invention is shown in Table 2.

TABLE 2

| $ED_{50}$ (*S. aureus* UC9213, sq) (mg/kg) | |
|---|---|
| Example No. 1 | 9.3 |
| Vancomycin (control) | 1.9 |

As such, the compounds of the present invention are useful for treating microbial infections in humans or other warm-blooded animals by administering to a patient in need thereof an effective amount of a compound of Formula I. The compound is administered in a pharmaceutical composition orally, parenterally (e.g., subcutaneously (sq) or intravenously) or topically. Preferably the compound is administered in an amount of from about 0.1 to about 100 mg/kg of body weight/day, more preferably, from about 3.0 to about 50 mg/kg of body weight/day.

The following compounds of the present invention are preferred:

Acetamide, N-[[4-[3-fluoro-4-(4-morpholinyl)phenyl]-2,5-dihydro-5-oxo-2-furanyl}methyl]-, (R)-; and Acetamide, N-[[4-[4-[4-(2-methoxy)-5-oxo-1,3,6-cycloheptatrien-1-yl]phenyl]-2,5-dihydro-5-oxo-2-furanyl]methyl]-.

DESCRIPTION OF PREFERRED EMBODIMENTS

Preparation 1 2-(4-Bromophenyl)-4-pentenoic Acid (Formula XIII-B) Refer to Chart XIII A solution of 4-bromophenylacetic acid (12.0 g) of Formula XIII-A in 450 ml of anhydrous THF is cooled to 0° C. via an ice bath. The solution is treated with lithium bis (trimethylsilyl)amide (LiHMDS, 1.0M in THF, 112 ml) which initially results in a light yellow slurry which becomes an orange homogeneous solution. The solution is stirred at 0° C. for 2 hrs followed by warming to room temperature. The solution is recooled to 0° C. and is treated dropwise with allyl bromide (5.0 ml). The mixture is left to stir overnight with gradual warming to room temperature. After 18 hrs the mixture is cooled to 0° C. and quenched with 250 ml of 10% aqueous HCl. The mixture is poured into a separatory funnel and extracted with EtOAc (2×300 ml). The combined organic extracts are dried over anhydrous $Na_2SO_4$, filtered and concentrated to give a viscous oil. This material is distilled (0.5 mm Hg, collected 158°–161° C.) to give 10.1 g of the title product.

Physical characteristics are as follows:

MS (EI): m/z: 254,256 [M$^+$], 215, 213, 211, 209, 134.

Preparation 2 Iodide, [[4-(4-bromophenyl) tetrahydro-5-oxo-2-furanyl]methyl]- (Formula XIII-C) Refer to Chart XIII 2-(4-Bromophenyl)-4-pentenoic acid (9.3 g) of Preparation 1 is dissolved into 35 ml of $Et_2O$ and the solution is cooled to 0° C. via an ice bath. Next 100 ml of saturated aqueous $NaHCO_3$ is added followed by dropwise addition of a THF solution (100 ml) of iodine (18.5 g). This mixture is stirred overnight under $N_2$ with gradual warming to room temperature. After 16 hrs the reaction mixture is treated with 200 ml of saturated sodium thiosulfate. This mixture is poured into a separatory funnel along with EtOAc (250 ml) and water (100 ml). The mixture is shaken and the organic phase is separated. The aqueous phase is extracted with additional EtOAc (300 ml). The combined organic extracts are washed with brine, dried over anhydrous $Na_2SO_4$ and concentrated to give the crude product that is purified by chromatography eluting with 7:1 hexane/EtOAc. This results in the isolation of two diastereomeric products. 3.23 g of higher $R_f$ (trans-) title product and 6.77 g of lower $R_f$ (cis-) title product are isolated.

Physical characteristics are as follows:

MP (trans-): 86°–88° C.; MP (cis-): 91°–93° C.

MS of mixture (EI): m/z: 380,382 [M$^+$], 211, 209, 130, 115, 77.

Preparation 3 Azide, [[4-(4-bromophenyl) tetrahydro-5-oxo-2-furanyl]methyl]- (Formula XIII-D) Refer to Chart XIII The iodide of Preparation 2 (1.3 g) is dissolved into 8 ml of dry DMF and the solution is treated with sodium azide (1.1 g) followed by heating to 60° C. under $N_2$. After 3.5 hrs the mixture is cooled to room temperature and TLC shows starting material is consumed. The DMF is removed under reduced pressure and the residue is slurried into $CH_2Cl_2$. The mixture is washed with water and brine. The organic phase is separated and dried over anhydrous $Na_2SO_4$. The solution is filtered and concentrated to give a viscous gum that is purified by chromatography on silica gel eluting with 4:1 hexane/EtOAc. This results in the isolation of two diastereomeric products. 256 mg of higher $R_f$ (trans-) azide as an oil and 431 mg of lower $R_f$ (cis-) title product as a waxy solid (MP=81°–83° C.) are isolated.

Physical characteristics are as follows:

MS of mixture (EI): m/z: 295,297 [M$^+$], 211, 213, 183, 185, 116, 104, 103, 77.

Preparation 4 Acetamide, N-[[4-(4-bromophenyl) tetrahydro-5-oxo-2-furanyl]methyl]- (Formula XIII-E) Refer to Chart XIII The azide of Preparation 3 (950 mg) is dissolved into 20 ml of dry THF and the solution is treated with $PPh_3$ (926 mg) in 3 portions. Gas evolution is observed during the addition. The mixture is stirred at room temperature for 16 hrs. After this time TLC shows the starting material is consumed with the formation of the baseline iminophosphorane. The reaction mixture is treated with 1.0 ml of water and heated to reflux for 3 hrs. After this time the mixture is cooled to room temperature and stirred for 16 hrs. The reaction mixture is diluted with benzene (100 ml) and the solution is concentrated under reduced pressure to give a viscous oil. The oil is dried at 0.4 mm Hg for 2 hrs and dissolved into 20 ml of dry $CH_2Cl_2$. The solution is cooled to 0° C., treated with pyridine (1.0 ml) and acetic anhydride (492 mg). The mixture is stirred with warming to room temperature. The reaction is poured into a separatory funnel and diluted with $CH_2Cl_2$. The solution is washed with 10% aqueous HCl, saturated $NaHCO_3$ and brine. The organic phase is concentrated to give a gum that is purified by radial chromatography eluting with MeOH/$CHCl_3$ mixture (1 to 4% MeOH in 200 ml volumes). Isolated 561 mg of title product as a white solid which is a mixture of inseparable diastereomers.

Physical characteristics are as follows:

MP: 167°–169° C.

MS of mixture (EI): m/z: 311, 313 [M$^+$], 271, 269, 183, 129, 104, 85, 72.

Preparation 5 Acetamide, N-[[4-(4-bromophenyl) tetrahydro-4-bromo-5-oxo-2-furanyl]methyl]- (Formula XIII-F) Refer to Chart XIII The acetamide starting material (1.0 g) of Preparation 4 is slurried into 25 ml of $CCl_4$. The slurry is treated with N-bromosuccinimide (713 mg) and benzoylperoxide (39 mg). The reaction mixture is degassed by evacuation and flushing with $N_2$ three times. The reaction mixture is heated to reflux for one hour followed by cooling to room temperature. After this time TLC shows a small quantity of starting material remains along with 2 new higher $R_f$ spots. The reaction mixture is concentrated under reduced pressure and the orange residue is dissolved in $CH_2Cl_2$ and filtered through a short pad of silica gel eluting with 4% MeOH/$CHCl_3$. The filtrate is concentrated and the residue is purified by radial chromatography eluting with 3% MeOH/$CHCl_3$. 540 mg of title product which is contaminated with succinimide is isolated. Also isolated 312 mg of starting material which is also contaminated with a small amount of succinimide. Upon repeated chromatography the succinimide is still present. This material is used as obtained.

Physical characteristics are as follows:

MS (EI): m/z: 311, 309, 252, 250, 240, 238, 102, 72, 43, 30.

Preparation 6 Acetamide, N-[[4-[4-bromophenyl]-2,5-dihydro-5-oxo-2-furanyl]methyl]- (Formula XIII-G) Refer to Chart XIII The dibromide starting material (230 mg) of Preparation 5 is dissolved into 1.0 ml of dry $CH_2Cl_2$ and 4.0 ml of dry toluene is added. The reaction mixture is treated with dry pyridine (198 mg) followed by heating to 80° C. After 3.5 hrs. TLC shows a new slightly lower $R_f$ product and starting material is consumed. The reaction mixture is concentrated to give a solid that is dissolved into $CH_2Cl_2$. The solution is washed with water and brine followed by drying over anhydrous $Na_2SO_4$. The solution is filtered and concentrated to give a solid that is purified by radial chromatography on silica gel eluting with 2.5% $MeOH/CHCl_3$. 131 mg of title product as a white solid is isolated.

Physical characteristics are as follows:

MP: 186°–187° C.

MS (EI): m/z: 311, 309 [M+], 252, 250, 240, 238, 159, 102, 72, 51.

EXAMPLE 1

Acetamide, N-[[4-[4-[4-(2-methoxy)-5-oxo-1,3,6-cycloheptatrien-1-yl]phenyl]-2,5-dihydro-5-oxo-2-furanyl]methyl]- (Formula XIII-H) Refer to Chart XIII The aryl bromide (100 mg) of Preparation 6 is slurried into 10 ml of 1,4-dioxane. The tropyl stannane (120 mg) is added and the mixture is degassed by evacuation anf flushing with $N_2$ three times. The catalyst bis(triphenylphosphine)-palladium dichloride (22 mg) is added and the mixture is degassed a final time followed by heating to reflux. After 1 hour of reflux TLC shows the starting aryl bromide is consumed with the formation of a new lower $R_f$ product. After cooling the reaction mixture is filtered through celite and the filtrate is concentrated to give a yellow residue that is purified by radial chromatography eluting with 250 ml each of 1–3% $MeOH/CHCl_3$. This gives 75 mg of the title product as a light yellow solid.

Physical characteristics are as follows:

MP: 200°–201° C.

MS (EI): m/z: 365 [M+], 306, 294, 278, 266, 237, 165, 72.

FORMULA CHART

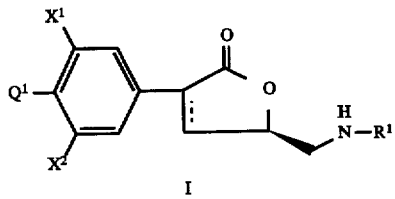

I

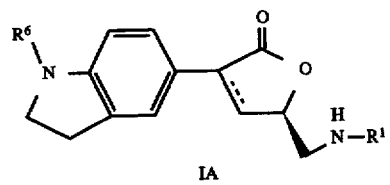

IA

FORMULA CHART -continued

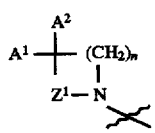

II

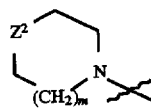

III

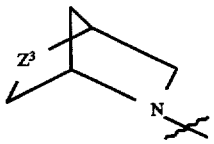

IV

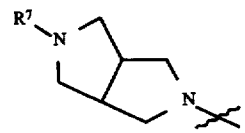

V

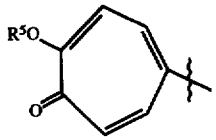

VI

VII

VIII

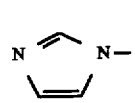

IX

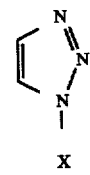

X

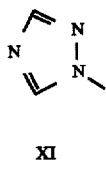

XI

XII

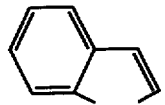

XIII

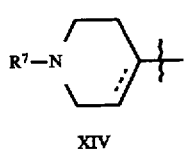

XIV

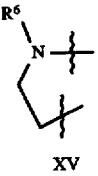

XV

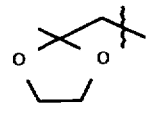

XVI

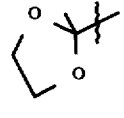

XVII

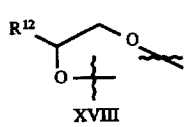

XVIII

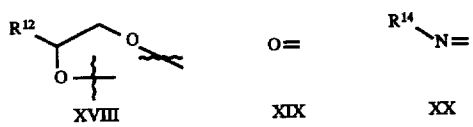

XIX

XX

-continued
FORMULA CHART

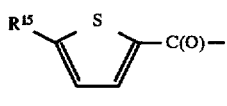

XXI

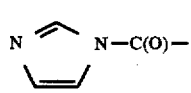

XXII

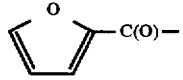

XXIII

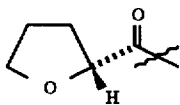

XXIV

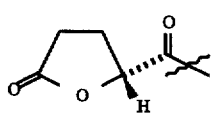

XXV

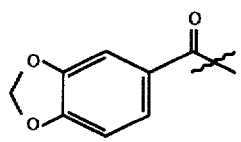

XXVI wherein Q¹ is

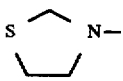  I-A

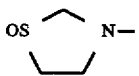  I-B

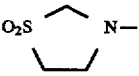  I-C

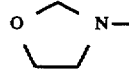  I-D wherein X¹ and X² are independently,
—H,
—F, or
—Cl;
wherein R¹ is
—CHO,
—COCH₃,
—COCHCl₂,
—COCHF₂,
—CO₂CH₃,
—SO₂CH₃, or
—COCH₂OH.

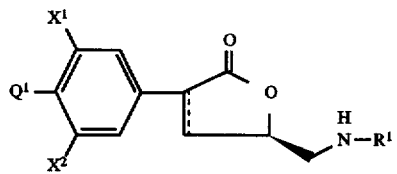  I wherein Q¹ is

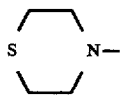  II-A

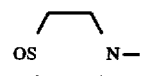  II-B

  II-C

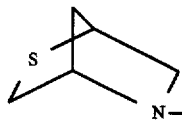  II-D

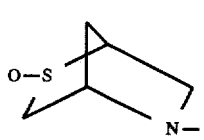  II-E

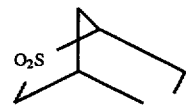  II-F wherein X¹ and X² are independently
—H,
—F, or
—Cl,
wherein R¹ is
—CHO,
—COCH₃,
—COCHCl₂,
—COCHF₂,
—CO₂CH₃,
—SO₂CH₃, or
—COCH₂OH.

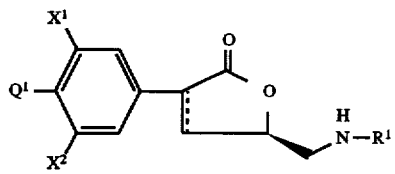  I wherein Q¹ is

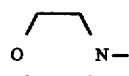  III-A

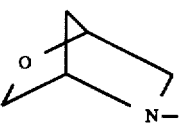  III-B wherein X¹ and X² are independently
—H,
—F, or
—Cl,
wherein R¹ is
—CHO,
—COCH₃,
—COCHCl₂, —COCHF₂,
—CO₂CH₃,
—SO₂CH₃, or
—COCH₂OH.
CHART IV - AZETIDINES
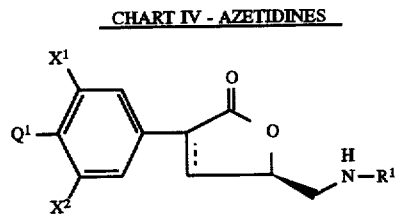
I
wherein Q¹ is
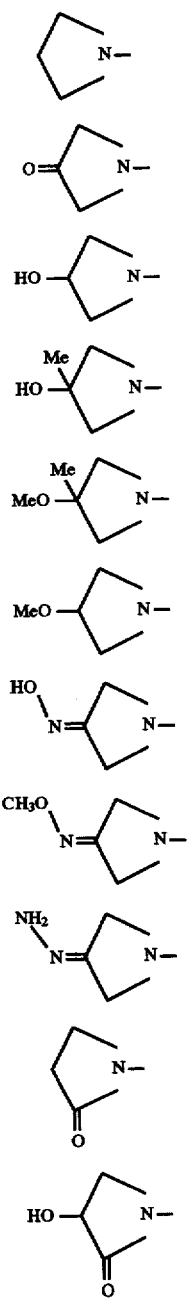
IV-A
IV-B
IV-C
IV-D
IV-E
IV-F
IV-G
IV-H
IV-I
IV-J
IV-K
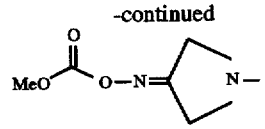
IV-L
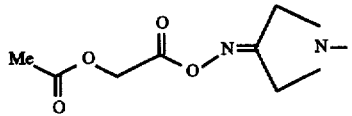
IV-M
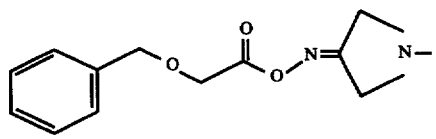
IV-N
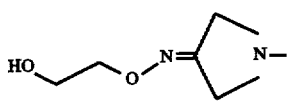
IV-O
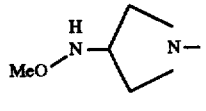
IV-P
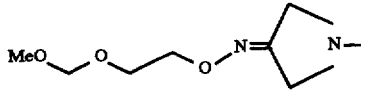
IV-Q
MeO—O—O—N= [N—]  IV-R
MeOMeO—O—N=  [N—]
wherein X¹ and X² are
  —H,
  —F, or
  —Cl;
wherein R¹ is
  —CHO,
  —COCH₃,
  —COCHCl₂,
  —COCHF₂,
  —CO₂CH₃,
  —SO₂CH₃, or
  —COCH₂OH.
I
wherein Q¹ is
V-A
V-B -continued
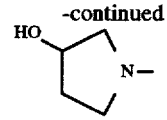 V-C
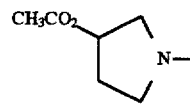 V-D
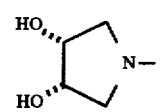 V-E
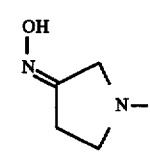 V-F
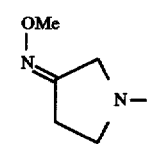 V-G
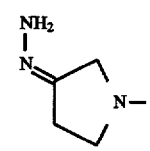 V-H
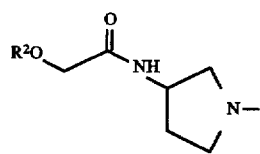 V-I
R² = H, Me
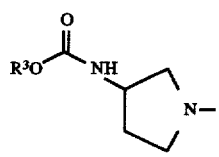 V-J
R³ = Me, Et, Pr
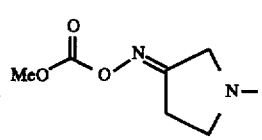 V-K
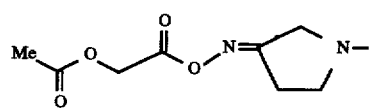 V-L
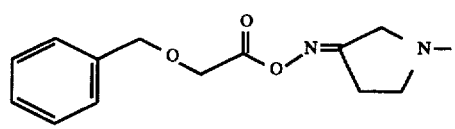 V-M
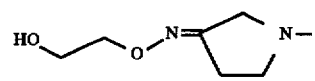 V-N
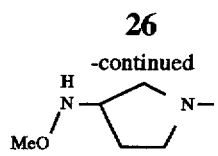 V-O
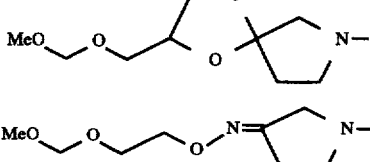 V-P
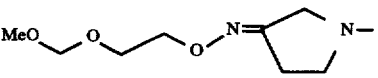 V-Q
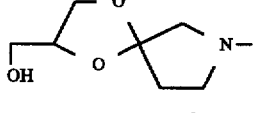 V-R
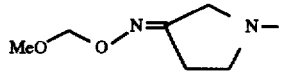 V-S
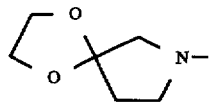 V-T
wherein $X^1$ and $X^2$ are independently
— H,
— F, or
— Cl;
wherein $R^1$ is
— CHO,
— COCH$_3$,
— COCHCl$_2$,
— COCHF$_2$,
— CO$_2$CH$_3$,
— SO$_2$CH$_3$, or
— COCH$_2$OH.
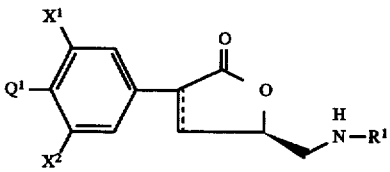 I
wherein $Q^1$ is
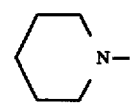 VI-A
 VI-B
 VI-C
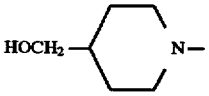 VI-D -continued VI-E, VI-F, VI-G, VI-H, VI-I, VI-J, VI-K, VI-L, VI-M, VI-N, VI-O, VI-P, VI-Q, VI-R, VI-S, VI-T, VI-U, VI-V, VI-W, VI-X, VI-Y, VI-Z, VI-A-1, VI-B-1, VI-C-1, VI-D-1

R⁴ = Me, Et

-continued

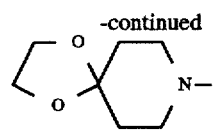

wherein $X^1$ and $X^2$ are independently
—H,
—F, or
—Cl;
wherein $R^1$ is
—CHO,
—COCH$_3$,
—COCHCl$_2$,
—COCHF$_2$,
—CO$_2$CH$_3$,
—SO$_2$CH$_3$, or
—COCH$_2$OH.

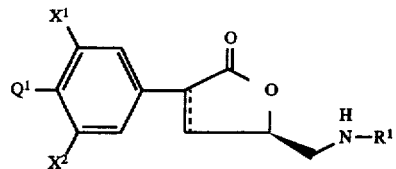

wherein $Q^1$ is

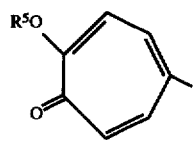

wherein $R^5$ is
H—, VII-A
CH$_3$—, VII-B
CH$_3$CH$_2$—, VII-C
(CH$_3$)$_2$CH—, VII-D
CH$_2$=CH—CH$_2$—, or VII-E
CH$_3$—O—CH$_2$—CH$_2$—; VII-F
wherein $X^1$ and $X^2$ are independently
—H,
—F, or
—Cl;
wherein $R^1$ is
—CHO,
—COCH$_3$,
—COCHCl$_2$,
—COCHF$_2$,
—CO$_2$CH$_3$,
—SO$_2$CH$_3$, or
—COCH$_2$OH.

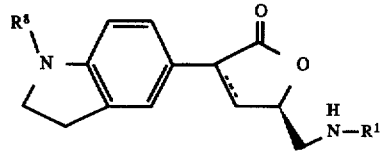

IA wherein $R^6$ is

 VIII-A

 VIII-B

Cl$_2$CHCO— VIII-C

HOCH$_2$CO— VIII-D

MeSO$_2$— VIII-E

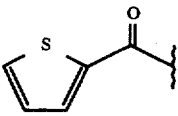 VIII-F

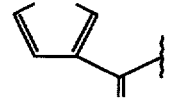 VIII-G

F$_2$CHCO— VIII-H

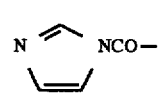 VIII-I

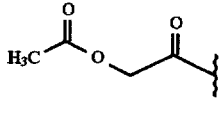 VIII-J

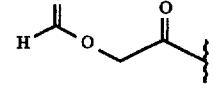 VIII-K

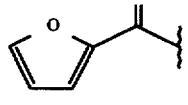 VIII-L

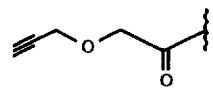 VIII-M

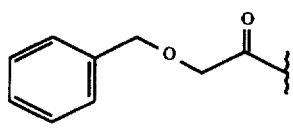 VIII-N

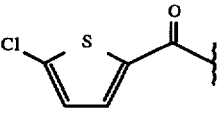 VIII-O wherein $R^1$ is
—CHO, VIII-P
—COCH$_3$, VIII-Q
—COCHCl$_2$, VIII-R
—COCHF$_2$, VIII-S
—CO$_2$CH$_3$, VIII-T
—SO$_2$CH$_3$, or VIII-U —COCH₂OH. VIII-V
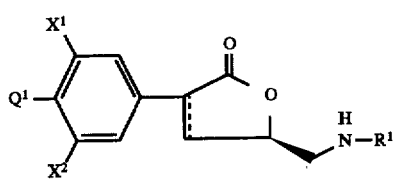
wherein Q¹ is
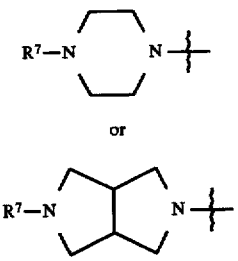
or
wherein R⁷ is
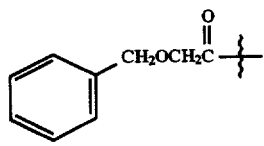 IX-A
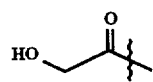 IX-B
 IX-C
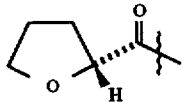 IX-D
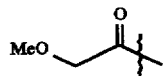 IX-E
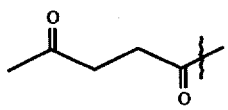 IX-F
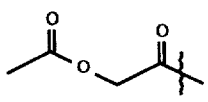 IX-G
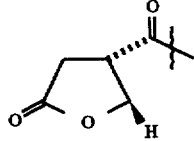 IX-H
MeSO₂— IX-I
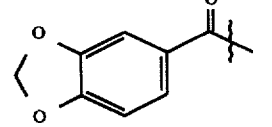 IX-J
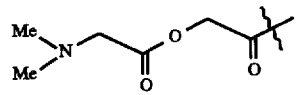 IX-K
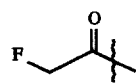 IX-L
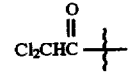 IX-M
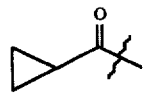 IX-N
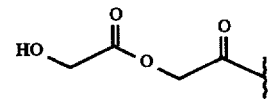 IX-O
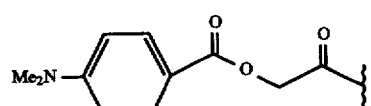 IX-P
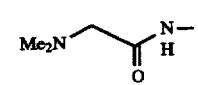 IX-Q
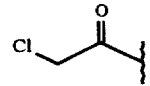 IX-R
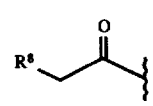 IX-S
R⁸ = F, Cl
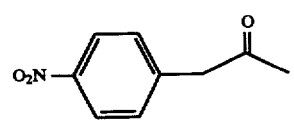 IX-T
 IX-U
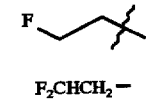 IX-V
F₂CHCH₂— IX-W
 IX-X
 IX-Y

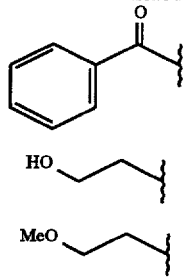

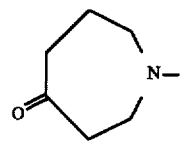

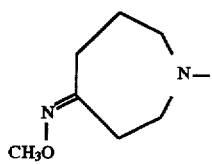

wherein $X^1$ and $X^2$ are independently
—H,
—F, or
—Cl;
wherein $R^1$ is
—CHO,
—COCH$_3$,
—COCHCl$_2$,
—COCHF$_2$,
—CO$_2$CH$_3$,
—SO$_2$CH$_3$, or
—COCH$_2$OH.

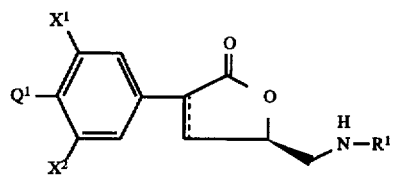

I wherein $Q^1$ is

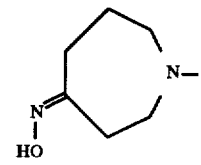 X-A

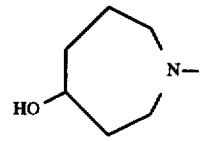 X-B

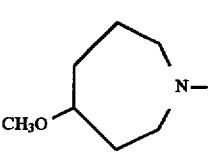 X-C

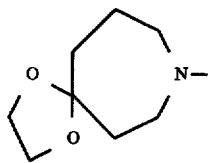 X-D

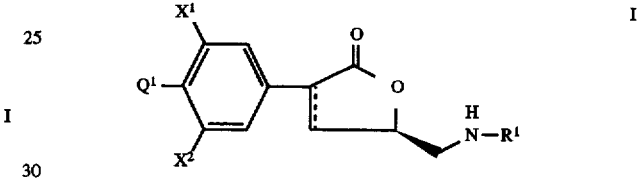 X-E

 X-F wherein $X^1$ and $X^2$ are independently
—H,
—F, or
—Cl;
wherein $R^1$ is
—CHO,
—COCH$_3$,
—COCHCl$_2$,
—COCHF$_2$,
—CO$_2$CH$_3$,
—SO$_2$CH$_3$, or
—COCH$_2$OH.

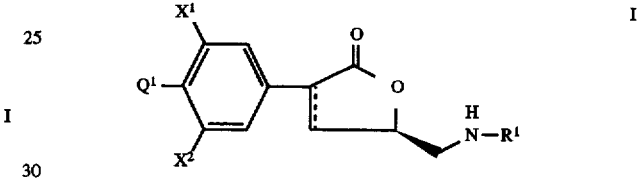

I wherein $Q^1$ is

 XI-A

 XI-B

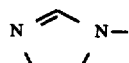 XI-C

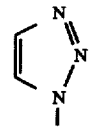 XI-D

 XI-E

 XI-F

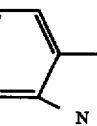 XI-G wherein $X^1$ and $X^2$ are independently

—H,
—F, or
—Cl;
wherein $R^1$ is
—CHO,
—COCH$_3$,
—COCHCl$_2$,
—COCHF$_2$,
—CO$_2$CH$_3$,
—SO$_2$CH$_3$, and
—COCH$_2$OH.
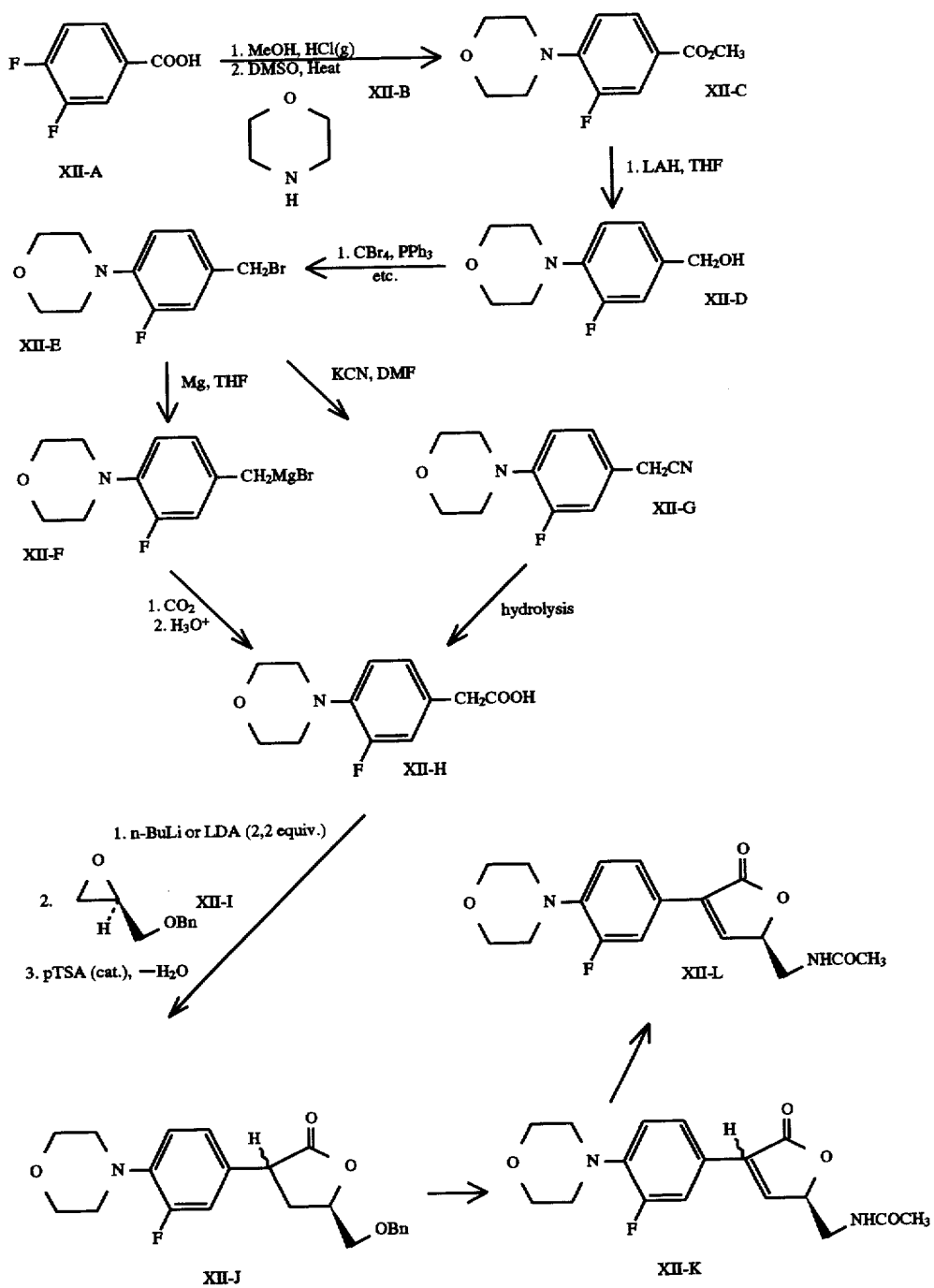
CHART XII -continued
CHART XII
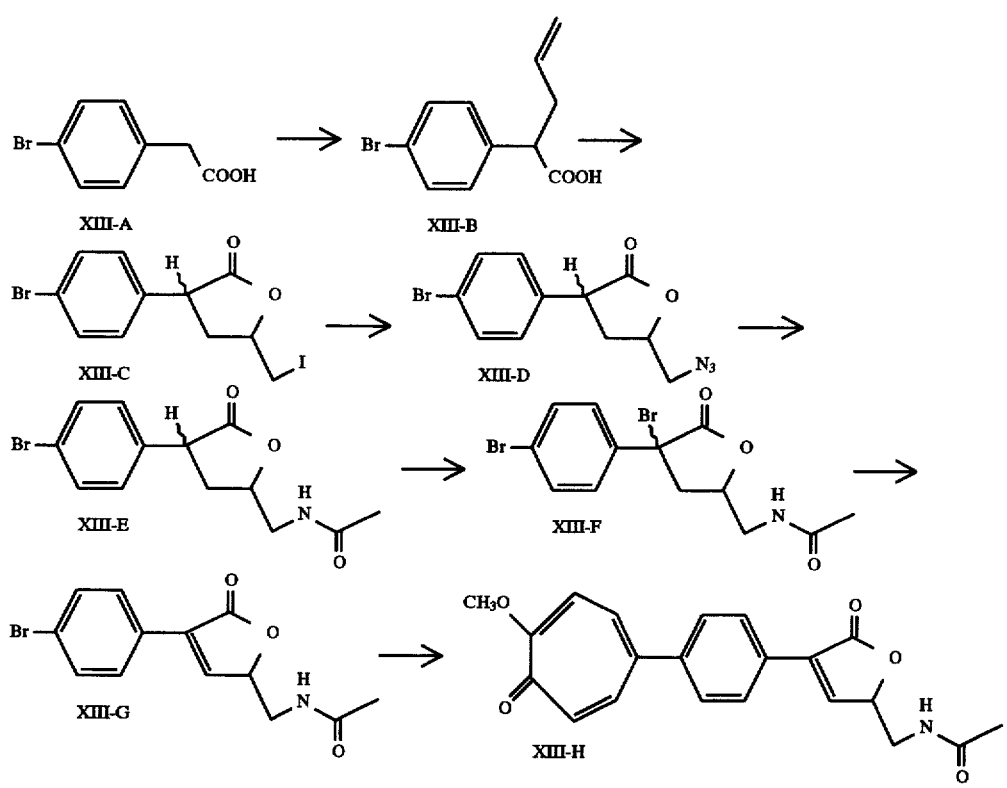
We claim:
1. A compound of the formula I
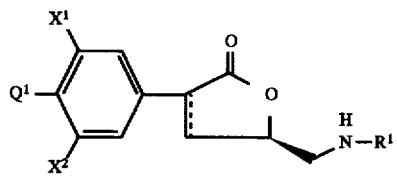
wherein --- is a single or double bond;
wherein $X^1$ and $X^2$ are independently
—H,
—F, or
—Cl;
wherein $Q^1$ is:
a) 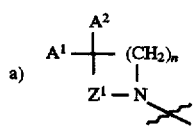  II
b) 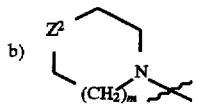  III
c) 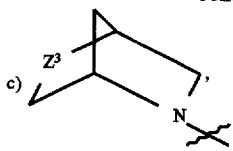  IV
d) 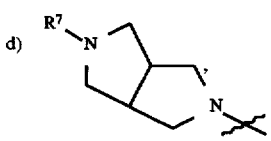  V
e) 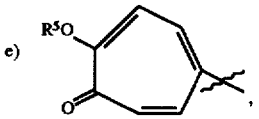  VI
f) 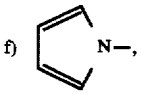  VII
g) 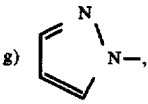  VIII
h) 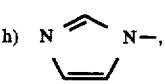  IX i) 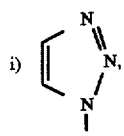

j) 

k) 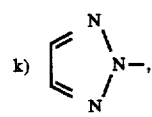

l) 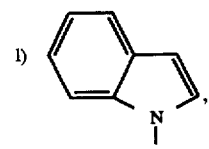

m) 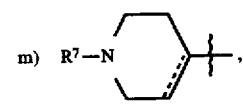

$Q^1$ and $X^2$ taken together are

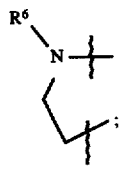

wherein $Z^1$ is
a) —$CH_2$—,
b) —$CH(R^4)$—$CH_2$—,
c) —$C(O)$—, or
d) —$CH_2CH_2CH_2$—;
wherein $Z^2$ is
a) —$O_2S$—,
b) —O—,
c) —$N(R^7)$—,
d) —OS—, or
e) —S—;
wherein $Z^3$ is
a) —$O_2S$—,
b) —O—,
c) —OS—, or
d) —S—;
wherein $A^1$ is
a) H—, or
b) $CH_3$;
wherein $A^2$ is
a) H—,
b) HO—,
c) $CH_3$—,
d) $CH_3O$—,
e) $R^2O$—$CH_2$—$C(O)$—NH—
f) $R^3O$—$C(O)$—NH—,
g) ($C_1$-$C_2$)alkyl-O—$C(O)$—, h) HO—$CH_2$—,
i) $CH_3O$—NH—,
j) ($C_1$-$C_3$)alkyl-$O_2C$—
k) $CH_3$—$C(O)$—,
l) $CH_3$—$C(O)$—$CH_2$—, m) 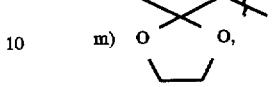

n) 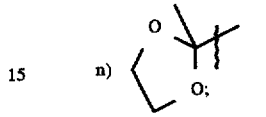

$A^1$ and $A^2$ taken together are:

a) 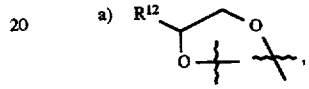

b) O=, or c) 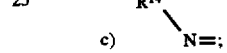

wherein $R^1$ is
a) —CHO,
b) —$COCH_3$,
c) —$COCHCl_2$,
d) —$COCHF_2$,
e) —$CO_2CH_3$,
f) —$SO_2CH_3$, or
g) —$COCH_2OH$;
wherein $R^2$ is
a) H—,
b) $CH_3$—,
c) phenyl-$CH_2$—, or
d) $CH_3C(O)$—;
wherein $R^3$ is
a) ($C_1$-$C_3$)alkyl-, or
b) phenyl-;
wherein $R^4$ is
a) H—, or
b) HO—;
wherein $R^5$ is
a) H—,
b) ($C_1$-$C_3$)alkyl-,
c) $CH_2$=CH—$CH_2$—, or
d) $CH_3$—O—$(CH_2)_2$—;
wherein $R^6$ is
a) $CH_3$—$C(O)$—,
b) H—$C(O)$—,
c) $Cl_2CH$—$C(O)$—,
d) $HOCH_2$—$C(O)$—,
e) $CH_3SO_2$—, f)

g) $F_2CHC(O)$—, h) 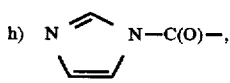

i) $H_3C$—$C(O)$—$O$—$CH_2$—$C(O)$—,
j) H—$C(O)$—$O$—$CH_2$—$C(O)$—, k) 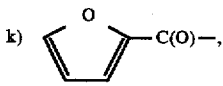

l) HC≡C—$CH_2$—$O$—$CH_2$—$C(O)$—, or
m) phenyl-$CH_2$—$O$—$CH_2$—$C(O)$—;
wherein $R^7$ is
  a) $R^2O$—$C(R_{10})(R_{11})$—$C(O)$—,
  b) $R^3O$—$C(O)$—,
  c) $R^8$—$C(O)$—, d) 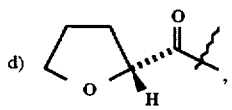

e) 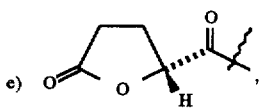

f) $H_3C$—$C(O)$—$(CH_2)_2$—$C(O)$—,
g) $R^9$—$SO_2$—, h) 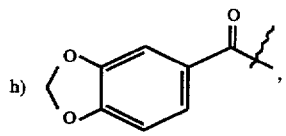

i) HO—$CH_2$—$C(O)$—,
j) $R^{16}$—$(CH_2)_2$—,
k) $R^{13}$—$C(O)$—$O$—$CH_2$—$C(O)$—,
l) $(CH_3)_2N$—$CH_2$—$C(O)$—NH—,
m) NC—$CH_2$—, or
n) $F_2$—CH—$CH_2$—;
wherein $R^8$ is
  a) H—,
  b) $(C_1-C_4)$alkyl,
  c) aryl —$(CH_2)_p$,
  d) $ClH_2C$—,
  e) $Cl_2HC$—,
  f) $FH_2C$—,
  g) $F_2HC$—, or
  h) $(C_3-C_6)$cycloalkyl;
wherein $R^9$ is
  a) —$CH_3$,
  b) —$CH_2Cl$
  c) —$CH_2CH=CH_2$,
  d) aryl, or
  e) —$CH_2CN$;
wherein $R^{10}$ and $R^{11}$ are independently
  a) H—,
  b) $CH_3$—; or
wherein $R^{12}$ is
  a) H—, b) $CH_3O$—$CH_2O$—$CH_2$—, or
c) $HOCH_2$—;
wherein $R^{13}$ is
  a) $CH_3$—,
  b) $HOCH_2$—,
  c) $(CH_3)_2N$-phenyl, or
  d) $(CH_3)_2N$—$CH_2$—;
wherein $R^{14}$ is
  a) HO—,
  b) $CH_3O$—,
  c) $H_2N$—,
  d) $CH_3O$—$C(O)$—$O$—,
  e) $CH_3$—$C(O)$—$O$—$CH_2$—$C(O)$—$O$—,
  f) phenyl-$CH_2$—$O$—$CH_2$—$C(O)$—$O$—,
  g) HO—$(CH_2)_2$—$O$—,
  h) $CH_3O$—$CH_2$—$O$—$(CH_2)_2$—$O$—, or
  i) $CH_3O$—$CH_2$—$O$—;
wherein $R^{15}$ is
  a) H—, or
  b) Cl—;
wherein $R^{16}$ is
  a) HO—
  b) $CH_3O$—, or
  c) F;
wherein m is zero (0) or one (1);
wherein n is one (1) to three (3), inclusive;
wherein p is zero (0) or one (1);
wherein aryl is phenyl substituted with zero (0) or one (1) of the following:
  a) —F,
  b) —Cl,
  c) —$OCH_3$,
  d) —OH,
  e) —$NH_2$,
  f) —$(C_1-C_4)$alkyl,
  g) —O—$C(O)$—$OCH_3$, or
  h) —$NO_2$;
or pharmaceutically acceptable salts thereof.

2. The compound of claim 1 with the following provisos:
1) in the moiety of formula II, when $Z^1$ is —$CH_2$— or —$C(O)$—, n is one (1);
2) in the moiety of formula II, when $Z^1$ is —$CH_2$—$CH_2$—$CH_2$—, n is not three (3).

3. The compound of claim 1 wherein $Q^1$ is the moiety of formula II.

4. The compound of claim 1 wherein $Q^1$ is the moiety of formula III.

5. The compound of claim 1 wherein $Q^1$ is the moiety of formula IV.

6. The compound of claim 1 wherein $Q^1$ is the moiety of formula V.

7. The compound of claim 1 wherein $Q^1$ is the moiety of formula VI.

8. The compound of claim 1 wherein $Q^1$ is the moiety of formula VII, VIII, IX, X, XI, XII, XIII, or XIV.

9. The compound of claim 1 selected from the group consisting of:
Acetamide, N-[[4-[3-fluoro-4-(4-morpholinyl)phenyl]-2,5-dihydro-5-oxo-2-furanyl]methyl]-, (R)-; and
Acetamide, N-[[4-[4-[4-(2-methoxy)-5-oxo-1,3,6-cycloheptatrien-1-yl]phenyl]-2,5-dihydro-5-oxo-2-furanyl]methyl]-.

* * * * *